(12) United States Patent
Tsai et al.

(10) Patent No.: US 9,492,426 B2
(45) Date of Patent: Nov. 15, 2016

(54) MYCOPHENOLIC ACID ANALOGUES AS ANTI-TUMOR CHEMOSENSITIZING AGENTS

(71) Applicant: Texas A & M University System, College Station, TX (US)

(72) Inventors: Robert Y. Tsai, Pearland, TX (US); Tao Lin, Houston, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 42 days.

(21) Appl. No.: 13/624,286

(22) Filed: Sep. 21, 2012

(65) Prior Publication Data

US 2014/0323507 A1 Oct. 30, 2014

Related U.S. Application Data

(60) Provisional application No. 61/537,379, filed on Sep. 21, 2011.

(51) Int. Cl.

| | |
|---|---|
| *A61K 31/365* | (2006.01) |
| *A61K 38/14* | (2006.01) |
| *A61K 45/06* | (2006.01) |
| *A61K 31/203* | (2006.01) |
| *A61K 31/337* | (2006.01) |
| *A61K 31/4745* | (2006.01) |
| *A61K 31/513* | (2006.01) |
| *A61K 31/555* | (2006.01) |
| *A61K 31/704* | (2006.01) |
| *A61K 31/7048* | (2006.01) |
| *A61K 31/282* | (2006.01) |

(52) U.S. Cl.
CPC .......... *A61K 31/365* (2013.01); *A61K 31/203* (2013.01); *A61K 31/282* (2013.01); *A61K 31/337* (2013.01); *A61K 31/4745* (2013.01); *A61K 31/513* (2013.01); *A61K 31/555* (2013.01); *A61K 31/704* (2013.01); *A61K 31/7048* (2013.01); *A61K 38/14* (2013.01); *A61K 45/06* (2013.01)

(58) Field of Classification Search
CPC .......... A61K 2300/00; A61K 31/513; A61K 31/555; A61K 31/7048; A61K 31/282; A61K 45/06
USPC .................................................. 514/274, 470
See application file for complete search history.

(56) References Cited

U.S. PATENT DOCUMENTS

2004/0092583 A1* 5/2004 Shanahan-Prendergast . 514/469
2014/0128408 A1* 5/2014 Kozikowski et al. ... 514/254.09

OTHER PUBLICATIONS

Sebaugh, J. L., "Guidelines for accurate EC50/1050 estimation", 2011, Pharmaceut. Statist., 10(2), pp. 128-134.*

* cited by examiner

*Primary Examiner* — My-Chau T Tran
(74) *Attorney, Agent, or Firm* — Winstead PC

(57) ABSTRACT

In some embodiments, the present invention provides methods of treating a tumor in a subject. In some embodiments, the methods may include a step of administering to the subject a therapeutic composition that comprises: (a) mycophenolic acid, an analog thereof, or a derivative thereof; and (b) at least one anti-neoplastic agent. In some embodiments, the antineoplastic agent may include at least one of 5-fluouracil (5-FU), paclitaxel, oxaliplatin, doxorubicin, etoposide, irinotecan, bleomycin, imiquimod, 13-cis-retinoic acid, and combinations thereof. In some embodiments, the relative concentrations of the mycophenolic acid, the analog thereof, or the derivative thereof, and the at least one anti-neoplastic agent correspond to their respective IC50 values. In some embodiments, the methods of the present invention may be used to treat tumors associated with at least one of an oral cancer, a skin cancer, a breast cancer, a prostate cancer, precancerous lesions thereof, hyperplastic lesions thereof, and benign tumors thereof.

17 Claims, 10 Drawing Sheets

MYCOPHENOLIC ACID ANALOGUES AS ANTI-TUMOR CHEMOSENSITIZING AGENTS

CROSS-REFERENCE TO RELATED APPLICATIONS

This application claims priority to U.S. Provisional Patent Application No. 61/537,379, filed on Sep. 21, 2011. The entirety of the aforementioned application is incorporated herein by reference.

BACKGROUND

Numerous high-grade malignancies and precancerous conditions exist that are difficult to treat, prevent and eradicate. Many of such conditions are affiliated with breast cancer, prostate cancer, skin cancer, oral cancer, and precancerous conditions thereof. Furthermore, current treatment methods have numerous limitations. Therefore, a need exists for the development of new methods and therapeutic compositions for treating various types of cancerous and precancerous conditions.

SUMMARY

In some embodiments, the present disclosure provides methods of treating a tumor in a subject. In some embodiments, the methods may include a step of administering to the subject a therapeutic composition that comprises: (a) mycophenolic acid, an analogue thereof, or a derivative thereof; and (b) at least one anti-neoplastic agent.

In some embodiments, the anti-neoplastic agent may include at least one of 5-fluouracil (5-FU), paclitaxel, oxaliplatin, doxorubicin, etoposide, irinotecan, bleomycin, imiquimod, 13-cis-retinoic acid, and combinations thereof. In some embodiments, the anti-neoplastic agent is 5-FU. In some embodiments, the anti-neoplastic agent includes taxanes (e.g. paclitaxel). In some embodiments, the anti-neoplastic agents are platinum complexes (e.g., cisplatin, carboplatin, and oxaliplatin).

In some embodiments, the mycophenolic acid is not derivatized. In some embodiments, the relative concentrations of the mycophenolic acid, the analogue thereof, or the derivative thereof and the at least one anti-neoplastic agent correspond to their respective $IC_{50}$ values. In some embodiments, the mycophenolic acid, the analogue thereof, or the derivative thereof and the least one anti-neoplastic agent are present at concentrations correlating to various ratios of their $IC_{50}$ values, such as 8:1; 6:1; 4:1; 3:1; 2:1; 3:2; 2:3; 1:2; 1:4; 1:6; or 1:8.

In some embodiments, the methods of the present disclosure may be used to treat tumors associated with at least one of an oral cancer, a skin cancer, a breast cancer, a prostate cancer, precancerous lesions thereof, hyperplastic lesions thereof, and benign tumors thereof. For instance, in some embodiments, the tumor to be treated is associated with at least one of an oral cancer, a precancerous oral lesion, or a hyperplastic oral lesion. In some embodiments, the tumor to be treated is associated with oral cancer, such as oral squamous cell carcinoma, carcinoma in situ, dysplastic oral cell carcinoma, melanoma, tetratoma, adenocarcinoma, lymphoma, and combinations thereof. In some embodiments, the oral cancer to be treated is oral squamous cell carcinoma. In some embodiments, the tumor to be treated is associated with hyperplastic oral lesions or precancerous oral lesions. In some embodiments, the tumor to be treated is associated with precancerous oral lesions, such as leukoplakia, erythroplakia, erythroleukoplakia, and combinations thereof.

In some embodiments, the tumor to be treated is associated with at least one of a skin cancer, a precancerous skin lesion, or a hyperplastic skin lesion. In some embodiments, the tumor to be treated is associated with skin cancer, such as squamous skin cell carcinoma, carcinoma in situ, basal cell carcinoma, melanoma, and combinations thereof. In some embodiments, the tumor to be treated is associated with hyperplastic skin lesions or precancerous skin lesions. In some embodiments, the tumor to be treated is associated with a precancerous skin lesion, such as actinic keratosis, actinic chelitis, cutaneous horns, warts, epidermodysplasia verruciformis, and combinations thereof.

In some embodiments, the tumor to be treated is associated with breast cancer, such as ductal carcinoma, lobular carcinoma, inflammatory breast cancer, metastatic breast cancer, adenocarcinoma, carcinosarcoma, and combinations thereof. In some embodiments, the tumor to be treated is associated with prostate cancer, such as adenocarcinoma, squamous cell carcinoma, small cell carcinoma, metastatic prostate cancer, and combinations thereof.

In some embodiments, the subject to be treated is a human being. In some embodiments, the human being may be suffering from one or more of the aforementioned cancerous or precancerous conditions.

In some embodiments, the therapeutic compositions of the present disclosure may be administered topically. In some embodiments, the topical administration may involve the use of carrier components, such as ointments, creams, gels, hydrogels, pastes, powders, patches, and combinations thereof. In some embodiments, the therapeutic compositions of the present disclosure may be administered systematically, such as through intravenous administration.

As set forth in more detail herein, the methods and therapeutic compositions of the present disclosure provide numerous treatment advantages. For instance, mycophenolic acid provides a synergistic effect against neoplastic cells when combined with an anti-neoplastic agent. In this way, it is believed that mycophenolic acid functions as a chemosensitizer to potentiate the anti-tumor activity of another antineoplastic agent.

DETAILED DESCRIPTION

Figure 1:
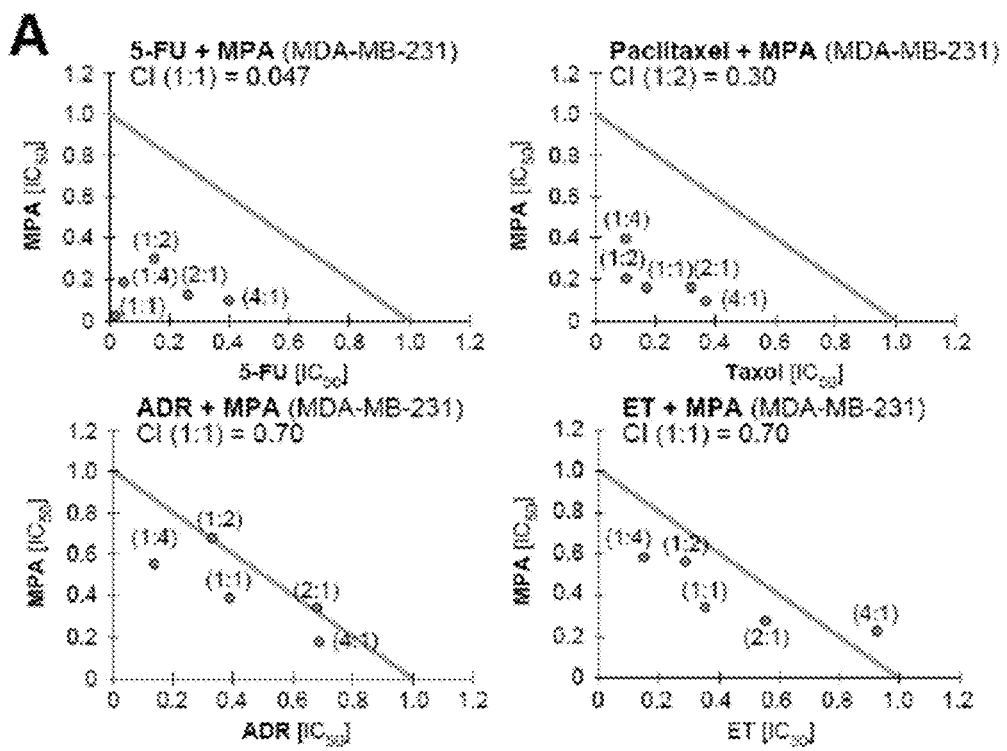
FIG. 1 shows data indicating that mycophenolic acid (MPA) and 5-fluorouracil (5-FU) have a strong synergistic effect on inhibiting the growth of MDA-MB-231 cells. The growth-inhibitory effect of combining MPA with 5-FU, paclitaxel, doxorubicin (ADR), and etoposide (ET) in MDA-MB-231 cells was determined by their combination indices (CI) calculated by isoborograms (FIG. 1A). For every drug combination, five different ratios of mixture (i.e. 4:1, 2:1, 1:1, 1:2, and 1:4) were tested, with the 1:1 combination representing each drug at their respective $IC_{50}$ concentrations. CI values less than 0.85 indicate a synergistic drug interaction. The combination of MPA and 5-FU at a 1:1 ratio shows the strongest synergy (CI=0.047). The synergy between 5-FU and oxaliplatin (OX) or irinotecan (IRI) was determined by the same approach (FIG. 1B). The 5-FU (0.15 ug/ml) plus MPA (0.19 uM) treatment shows a much stronger activity in inhibiting tumor cell proliferation, shown by the BrdU-labeled cell percentage, compared to the 5-FU alone (0.15 ug/ml) or MPA (0.19 uM) alone treatment (FIG. 1C). At later time points, cells treated with both 5-FU and MPA show a significant increase of TUNEL⁺ cells compared to non-treated cells and cells treated with 5-FU or MPA alone (FIG. 1D).
Figure 1:
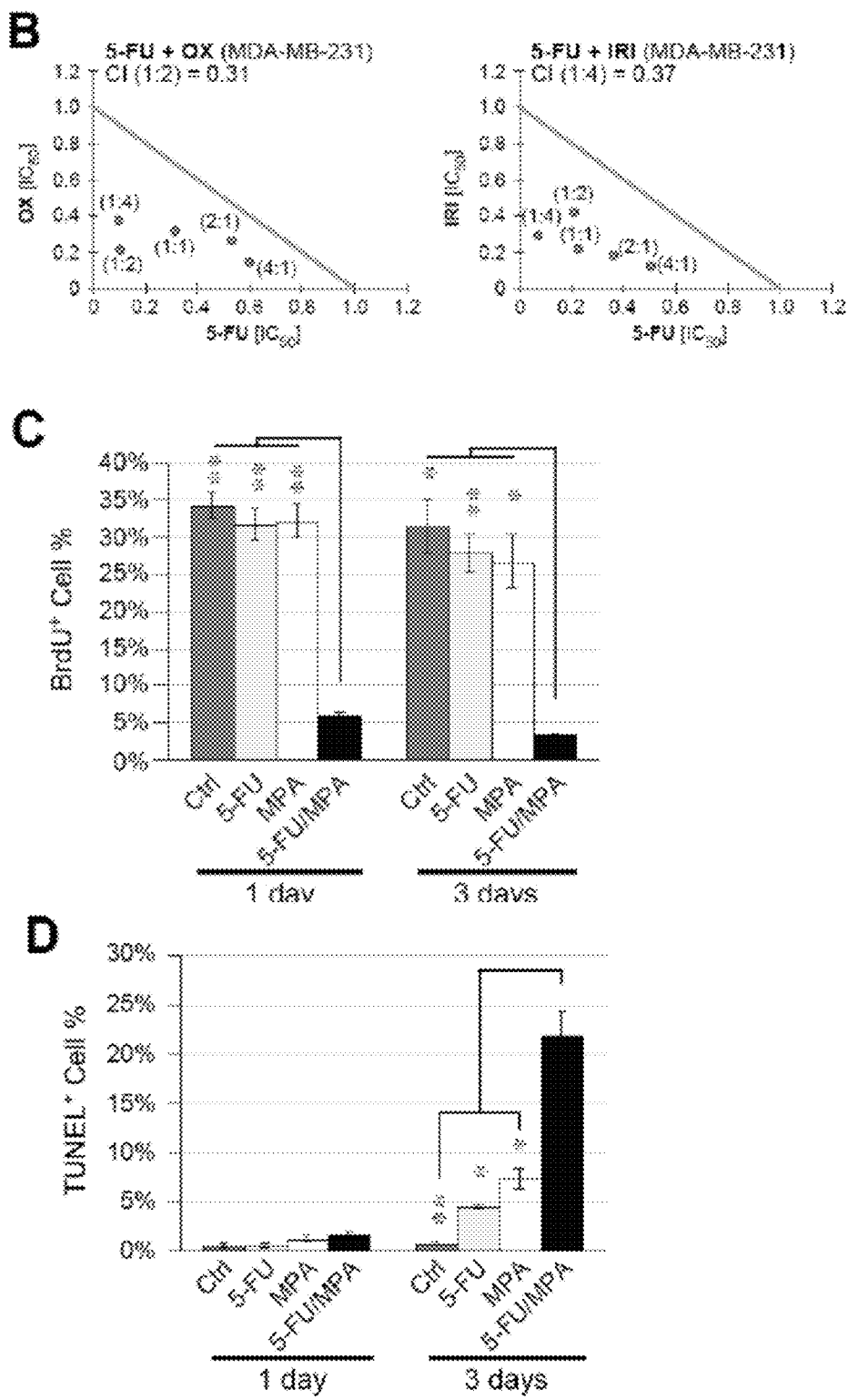

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Numerous high-grade malignancies and precancerous conditions exist that are difficult to treat, prevent and eradicate. Many of such conditions are affiliated with breast cancer, prostate cancer, skin cancer, oral cancer, and precancerous conditions thereof. Furthermore, current treatment methods have numerous limitations.

For instance, breast cancer is the most common form of neoplasm for women in the Western countries, trailing behind only lung cancer. Although continuous progress in early detection and treatment has been made, therapeutic options for the aggressive form of breast cancers (i.e., the triple-negative breast cancer (TNBC)), still remain very limited. Thus, there is an urgent need to explore new ideas and targets for breast cancer treatment.

Likewise, oral cancer is the 8th most common cancer in males and 15th in females in the US. The five-year survival rate of oral cancer (53% to 60%) is one of the lowest of all the major cancer types. Moreover, patients who survive oral cancer often have to live with impaired functions and sometimes disfiguration caused by the surgical or radiation treatment. For these reasons, oral cancer poses a major human health issue. The present disclosure aims to address the aforementioned needs in treating and preventing various types of cancers and precancerous conditions.

In some embodiments, the present disclosure generally relates to therapeutic combinations and methods for use thereof for treatment or prevention of premalignant and neoplasia disorders. In some embodiments, the present disclosure is based in part on the observation that mycophenolic acid (MPA) provides a synergistic effect against neoplastic cells when combined with an anti-neoplastic agent. In this way, it is believed that MPA functions as a chemosensitizer to potentiate the anti-tumor activity of another antineoplastic agent.

In some embodiments, the present disclosure provides methods of treating a tumor in a subject by administering to the subject a therapeutic composition that includes: (1) mycophenolic acid, an analogue thereof, or a derivative thereof; and (2) at least one anti-neoplastic agent. In some embodiments, the tumor may be associated with at least one of an oral cancer, a skin cancer, a breast cancer, a prostate cancer, precancerous lesions thereof, hyperplastic lesions thereof, and benign tumors thereof. As set forth in more detail herein, the methods of the present disclosure may utilize various therapeutic compositions to treat various types of tumors in various subjects through various modes of administration.

Therapeutic Compositions

In the present disclosure, therapeutic compositions generally include a mycophenolic acid, an analogue thereof, or a derivative thereof. The therapeutic compositions of the present disclosure also include one or more anti-neoplastic agents. As set forth in more detail herein, various mycophenolic acids and anti-neoplastic agents may be utilized at various concentrations.

Mycophenolic Acid

By way of background, mycophenolic acid has been used clinically as an immunosuppressive drug for organ transplant and psoriasis treatment. Its activity was first discovered in the *Penicillium glaucum* culture broth more than a century ago. It was not until 1969 that Birch and Wright reported its total synthesis. MPA was shown to reduce the de novo synthesis of guanosine nucleotide by inhibiting the rate-limiting enzyme in this pathway, inosine-monophosphate dehydrogenase. Impaired interconversion of inosine, xanthosine, and guanosine nucleotides decreases the RNA and DNA synthesis as well as the GTP/GDP level. Given that GTP also serves as a "universal" molecule that controls the "on" and "off" states of many GTP-binding proteins, MPA treatment is expected to exert a ubiquitous effect on cell proliferation.

A growing body of evidence supports the anti-cancer activity of MPA, despite that early studies did not conclude a significant anti-cancer efficacy of MPA in clinical trials. MPA has been shown to inhibit tumor growth via p53 activation, cyclin D3 and p27 inhibition, Ras-MAPK and mTOR inhibition, induction of caspase-dependent and independent apoptosis, and nucleostemin destabilization. One of the studies reported that imatinib and MPA can work synergistically to induce apoptosis in Bcr-Abl expressing cell lines.

In some embodiments, the therapeutic compositions of the present disclosure may include unmodified or underivatized forms of mycophenolic acid. In some embodiments, the therapeutic compositions of the present disclosure may include an analogue or a derivative of mycophenolic acid. In some embodiments, the therapeutic compositions of the present disclosure may include a combination of underivatized forms of MPA, MPA analogues, and MPA derivatives.

In some embodiments, the therapeutic compositions of the present disclosure may include one or more derivatives of mycophenolic acid. MPA derivatives generally refer to MPA molecules that have been functionalized or derivatized. Exemplary MPA derivatives include, without limitation, MPAs with modified side chains, MPAs with allylic substitutions, MPA salts (e.g., mycophenolate sodium), MPA prodrugs (e.g., mycophenolate mofetil), and the like. More specific examples of MPA derivatives may include, without limitation, euparvic acid, F01 1358B, F01 1358A, F13459, mycophenolic acids with adenine dinucleotides, C2-mycophenolic adenine dinucleotide, C4-mycophenolic adenine dinucleotide, C6-mycophenolic adenine dinucleotide, mycophenolic acid glucuronide, beta-methylene-mycophenolic adenine dinucleotide, mycophenolic adenine dinucleotide, mycophenolate mofetil, dextran T70-mycophenolic acid conjugate, ethyl O—(N-(4 carboxyphenyl)carbamoyl) mycophenolate, carbamoyl mycophenolic acid ethyl ester, and combinations thereof.

In some embodiments, the therapeutic compositions of the present disclosure may include one or more analogues of mycophenolic acid. MPA analogues generally refer to molecules that have the same properties or mechanism of action as MPA. In some embodiments, suitable MPA analogues may include, without limitation, ribavirin, AVN-9441, Tiazofurin, and combinations thereof.

Anti-Neoplastic Agents

Anti-neoplastic agents generally refer to agents that prevent the development, maturation, or spread of neoplastic cells (e.g., cancer cells). In some embodiments, antineoplastic agents refer to agents that control or kill neoplastic cells.

In some embodiments, the therapeutic compositions of the present disclosure may include one or more anti-neoplastic agents. In some embodiments, suitable anti-neoplastic cells include, without limitation, 5-fluouracil (5-FU), paclitaxel, oxaliplatin, doxorubicin, etoposide, irinotecan, bleomycin, imiquimod, 13-cis-retinoic acid, and combinations thereof. In some embodiments, the anti-neoplastic agent is 5-fluorouracil. In some embodiments, the anti-neoplastic agents include, without limitation, a thymidylate synthase inhibitor (e.g., 5-FU), a mitotic inhibitor (e.g., taxanes, such as paclitaxel, and vinca alkaloids), platinum complexes (e.g., cisplatin, carboplatin, and oxaliplatin), and combinations thereof. In some embodiments, the anti-neoplastic agents may include doxorubicin or etoposide.

Additional suitable anti-neoplastic agents may include, without limitation, acitretin, aldesleukin, ambrisentan, alefacept, alitretinoin, altretamine, amsacrine, anastrozole, arsenic trioxide, asparaginase, azacitidine, azathioprine, bacillus calmette-guerin (BCG), bendamustine HCl, bexarotene, bicalutamide, bleomycin, bortezomib, bosentan, busulfan, cabergoline, capecitabine, carbamazepine, carboplatin, carmustine, cetrorelix acetate, chlorambucil, chloramphenicol, cidofovir, cisplatin, cladribine, clofarabine, clonazepam, colchicine, cyclophosphamide, cyclosporin, cytarabine, dacarbazine, dactinomycin, dasatinib, daunorubicin HCl, decitibine, degarelix, denileukin, diethylstilbestrol, dinoprostone, docetaxel, doxorubicin, dronedarone HCl, dutasteride, entecavir, epirubicin, ergonovine/methylergonovine, estradiol, estramustine phosphate, estrogen-progestin combinations, estrogens, estrone, estropipate, everolimus, exemestane, finasteride, floxuridine, fludarabine, fluoxymesterone, flutamide, fulvestrant, ganciclovir, ganirelix acetate, gemcitabine, gemtuzumab ozogamicin, gonadotropin, chorionic, goserelin, hydroxyurea, idarubicin, ifosfamide, imatinib mesylate, irinotecan HCl, ixabepilone, leflunomide, lenalidomide, letrozole, leuprolide acetate, lomustine, mechlorethamine, medroxyprogesterone acetate, megestrol, melphalan, menotropins, mercaptopurine, methotrexate, methyltestosterone, mifepristone, mitomycin, mitotane, mitoxantrone HCl, mycophenolate mofetil, mycophenolic acid, nafarelin, nelarabine, nilotinib, nilutamide, oxaliplatin, oxcarbazepine, oxytocin, palifermin, paroxetine, pazopanib HCl, pegaspargase, pemetrexed, pentamidine isethionate, pentetate calcium trisodium, pentostatin, phenoxybenzamine HCl, pipobroman, plerixafor, podofilox, podophyllum resin, pralatrexate, procarbazine, progesterone, progestins, raloxifene, rasagiline mesylate, ribavirin, risperidone, romidepsin, sirolimus, sorafenib, streptozocin, sunitinib malate, tacrolimus, tamoxifen, televancin, temozolomide, temsirolimus, teniposide, testolactone, testosterone, tetracycline HCl, thalidomide, thioguanine, thiotepa, topotecan, toremifene citrate, tretinoin, trifluridine, triptorelin, uracil mustard, valganciclovir, valproic acid/divalproex Na, valrubicin, vidarabine, vigabatrin, vinblastine sulfate, vincristine sulfate, vinorelbine tartrate, vorinostat, zidovudine, ziprasidone HCl, zoledronic acid, zonisamide, and combinations thereof.

Synergistic Effects

In some embodiments, the MPA (including derivatives or analogs) and the anti-neoplastic agent may be administered to a subject in an amount sufficient to have a strong, moderate or mild synergistic effect. In some embodiments, a synergistic effect refers to a combination index (CI) less than or equal to 0.85. In some embodiments, strong, moderate, and mild synergism may be defined by CI values of 0.1~0.3, 0.3~0.7, and 0.7~0.85, respectively.

Certain synergistic combinations of MPA (including derivatives or analogs) and an antineoplastic agent may be preferred for certain types of cancers. A particular combination may be determined by a person of ordinary skill in the art. For example, a synergistic combination of MPA and 5-FU may be used to treat breast cancer, prostate cancer, or skin cancer (e.g., squamous cell carcinoma). Likewise, a synergistic combination of MPA and paclitaxel may be used to treat skin cancer (e.g., squamous cell carcinoma) or breast cancer. Similarly, a synergistic combination of MPA and oxaliplatin may be used to treat skin cancer (e.g., squamous cell carcinoma). Likewise, a synergistic combination of MPA and doxorubicin, or a synergistic combination of MPA and etoposide may be used to treat breast cancer.

Ratios

Mycophenolic acids (including derivatives or analogs) and anti-neoplastic agents may be present in therapeutic compositions of the present disclosure at various concentrations. In some embodiments, the relative concentrations of the mycophenolic acid (including derivatives or analogs) and the anti-neoplastic agent may correspond to their respective half-inhibitory concentrations ($IC_{50}$ values) for a particular tumor type. Furthermore, the $IC_{50}$ concentrations for various drugs may vary depending on the tumor cell types.

In some embodiments, the mycophenolic acid (including derivatives or analogs) and the anti-neoplastic agent may be present at various concentrations that correlate to their $IC_{50}$ values. In some embodiments, the concentration ratios of the mycophenolic acid (including derivatives or analogs) to the least one anti-neoplastic agent may include at least one of 8 times the $IC_{50}$ value: the $IC_{50}$ value (8:1); 6 times the $IC_{50}$ value:the $IC_{50}$ value (6:1); 4 times the $IC_{50}$ value: the $IC_{50}$ value (4:1); 3 times the $IC_{50}$ value: the $IC_{50}$ value (3:1); 2 times the $IC_{50}$ value: the $IC_{50}$ value (2:1); 3 times the $IC_{50}$ value:2 times the $IC_{50}$ value (3:2); 2 times the $IC_{50}$ value:3 times the $IC_{50}$ value (2:3); the $IC_{50}$ value:2 times the $IC_{50}$ value (1:2); the $IC_{50}$ value:4 times the $IC_{50}$ value (1:4); the $IC_{50}$ value: 6 times the $IC_{50}$ value (1:6); or the $IC_{50}$ value:8 times the $IC_{50}$ value (1:8). Additional concentration ratios can also be envisioned by persons of ordinary skill in the art.

Carrier Components

In various embodiments, the therapeutic compositions of the present disclosure may also be associated with a variety of well established carrier components. Carrier components generally refer to compounds or structures that, for instance, enhance the stability of the therapeutic composition, enhance or facilitate the delivery of the therapeutic composition to a desired site, or enhance the pharmacological properties of the therapeutic composition (e.g., increase in vivo half-life, reduce toxicity, etc.).

For instance, in some embodiments where topical administration of the therapeutic composition is desired, the carrier component may include at least one of ointments, creams, gels, hydrogels, pastes, powders, patches, and combinations thereof. In some embodiments, the carrier components may include one or more physiologically acceptable carriers or excipients. Suitable carriers and excipients may include, without limitation, amino acids (e.g., glycine, glutamine, asparagine, arginine and lysine); antimicrobials; antioxidants (e.g., ascorbic acid, sodium sulfite and sodium hydrogen-sulfite); buffers (e.g., borate, bicarbonate, Tris-HCl, citrates, phosphates and other organic acids); bulking agents (e.g., mannitol and glycine); chelating agents (e.g., ethylenediamine tetraacetic acid (EDTA)); complexing agents (e.g., caffeine, polyvinylpyrrolidone, beta-cyclodextrin, and hydroxypropyl-beta-cyclodextrin); fillers; monosaccharides, disaccharides, other carbohydrates (e.g., glucose, mannose and dextrins); proteins (e.g., serum albumin, gelatin and immunoglobulins); coloring, flavoring, and diluting agents; emulsifying agents; hydrophilic polymers (e.g., polyvinylpyrrolidone); low molecular weight polypeptides; salt-forming counterions (e.g., sodium); preservatives (e.g., benzalkonium chloride, benzoic acid, salicylic acid, thimerosal, phenethyl alcohol, methylparaben, propylparaben, chlorhexidine, sorbic acid and hydrogen peroxide); solvents (e.g., glycerin, propylene glycol and polyethylene glycol); sugar alcohols (e.g., mannitol and sorbitol); suspending agents; surfactants or wetting agents (e.g., pluronics, PEG, sorbitan esters, polysorbates); stability enhancing agents (e.g., sucrose and sorbitol); tonicity enhancing agents (e.g., alkali metal halides); delivery vehicles; diluents; excipients; and combinations thereof.

Tumors

The methods of the present disclosure may be used to treat various tumors. Tumors generally refer to abnormal masses of cells or tissues. In some embodiments, tumors may refer to precancerous lesions, hyperplastic lesions, premalignant tumors, benign tumors, malignant tumors, cancerous tumors, and combinations thereof. In some embodiments, the tumor to be treated may be associated with at least one of an oral cancer, a skin cancer, a breast cancer, a prostate cancer, precancerous lesions thereof, hyperplastic lesions thereof, or benign tumors thereof. In some embodiments, the methods of the present disclosure may be used to treat high-grade malignancies that are difficult to eradicate and resistant to conventional chemotherapeutic agents.

Oral Tumors

In some embodiments, the methods of the present disclosure may be utilized to treat various types of oral tumors. In some embodiments, the oral tumor may be associated with at least one of an oral cancer, a precancerous oral lesion, a hyperplastic oral lesion, or a benign oral tumor.

In some embodiments, the methods of the present disclosure may be used to treat tumors associated with oral cancer. In some embodiments, the oral cancer may include, without limitation, at least one of oral squamous cell carcinoma, carcinoma in situ, dysplastic oral cell carcinoma, melanoma, tetratoma, adenocarcinoma, lymphoma, and combinations thereof. In some embodiments, the oral cancer to be treated may include oral squamous cell carcinoma.

In some embodiments, the methods of the present disclosure may be used to treat hyperplastic oral lesions or precancerous oral lesions. In some embodiments, the methods of the present disclosure may be utilized to treat precancerous oral lesions. In some embodiments, the precancerous oral lesions to be treated may include, without limitation, leukoplakia, erythroplakia, erythroleukoplakia, and combinations thereof. In some embodiments, the tumor to be treated may contain dysplastic oral keratinocytes (DOK).

Skin Tumors

In some embodiments, the methods of the present disclosure may be utilized to treat various types of skin tumors. In some embodiments, the tumor may be associated with at least one of a skin cancer, a precancerous skin lesion, a hyperplastic skin lesion, or a benign skin tumor.

In some embodiments, the methods of the present disclosure may be utilized to treat tumors associated with skin cancer. In some embodiments, the skin cancer may include, without limitation, at least one of squamous skin cell carcinoma, carcinoma in situ, basal cell carcinoma, melanoma, and combinations thereof.

In some embodiments, the methods of the present disclosure may be utilized to treat hyperplastic skin lesions or precancerous skin lesions. In some embodiments, the methods of the present disclosure may be used to treat tumors associated with precancerous skin lesions. In some embodiments, the precancerous skin lesions may include, without limitation, at least one of actinic keratosis, actinic chelitis, cutaneous horns, warts, epidermodysplasia verruciformis, and combinations thereof.

Breast Tumors

In some embodiments, the methods of the present disclosure may also be used to treat various types of breast tumors. In some embodiments, the tumor may be associated with at least one of a breast cancer, a precancerous breast lesion, a hyperplastic breast lesion, or a benign breast tumor.

In some embodiments, the breast tumors may be associated with breast cancer. In some embodiments, the breast cancer may include, without limitation, at least one of ductal carcinoma, lobular carcinoma, inflammatory breast cancer, metastatic breast cancer, adenocarcinoma, carcinosarcoma, and combinations thereof.

Prostate Tumors

In some embodiments, the methods of the present disclosure may also be used to treat various types of prostate tumors. In some embodiments, the prostate tumor may be associated with at least one of a prostate cancer, a precancerous prostate lesion, a hyperplastic prostate lesion, or a benign prostate tumor.

In some embodiments, the prostate tumor may be associated with prostate cancer. In some embodiments, the prostate cancer may include, without limitation, at least one of adenocarcinoma, squamous cell carcinoma, small cell carcinoma, metastatic prostate cancer, and combinations thereof.

Subjects

The methods of the present disclosure may be used to treat tumors in various subjects. In some embodiments, the subjects may be human beings. In some embodiments, the subjects may be human beings suffering from one or more types of cancers, such as oral cancer, skin cancer, breast cancer, prostate cancer, and combinations thereof. In some embodiments, the subjects may be human beings with precancerous lesions, hyperplastic lesions, or benign tumors. In some embodiments, the subjects may be animals, such as mice, rats, rodents, and mammals.

Modes of Administration

The methods of the present disclosure may also utilize various modes of administration. In some embodiments, the administration may include topical administration. In more specific embodiments, therapeutic compositions utilized for topical administration may be associated with at least one carrier component, such as ointments, creams, gels, hydrogels, pastes, powders, and combinations thereof. In further embodiments, the topical administration may utilize a patch, such as a transdermal or transmucosal patch.

In further embodiments, the therapeutic compositions of the present disclosure may be administered to a subject systematically. In some embodiments, the systemic administration may include intravenous administration.

The therapeutic compositions of the present disclosure may also be administered by other modes of administration that are known to persons of ordinary skill in the art. Such modes of administration may include, without limitation, oral administration, inhalation, subcutaneous (sub-q), intraperitoneal (I.P.), intramuscular (I.M.), or intrathecal injection. In some embodiments, the therapeutic compositions of the present disclosure may also be administered by controlled release mechanisms, or by delivery devices that are well-known to those of ordinary skill in the art.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1

Synergistic Inhibition of Breast and Oral Cancer Cells

In this Example, Applicants demonstrate that the combination of MPA and 5-FU synergistically inhibits the growth of various types of breast cancer cells. Applicants also demonstrate in this Example that the combination of MPA and paclitaxel synergistically inhibit the growth of oral cancer cells.

Materials and Methods

Animals

All animals were housed in the Program of Animal Resources in Texas A&M Health Sciences Center (TAMHSC)-Houston and handled in accordance with the principles and procedure of the Guide for the Care and Use of Laboratory Animals. All animal procedures were approved by the Institutional Animal Care and Use Committee (#10009 and #10010).

Cell Culture

Human cancer cells were obtained from ATCC and maintained in DMEM or DMEM/F12, supplemented with 10% FBS (Hyclone), penicillin (50 Mimi), streptomycin (50 ug/ml), and glutamine (1%). For primary culture, mammary tumor cells were harvested from MMTV-wnt-1/FVB/NJ female transgenic mice (Jackson Laboratory). After harvest, tumor tissues were minced and digested with collagenase and hyaluronidase, filtered through 40 µm Nylon mesh, and grown in DMEM/F12, supplemented with apo-transferrin, selenium, insulin, FGF2 (10 ng/ml), and EGF (20 ng/ml) in adherent or suspension (tumor sphere) culture. Fresh FGF2 and EGF were added daily. Medium change was done on a 3-day schedule.

Doxycycline-Inducible NS-Knockdown Stable Cells

An NS-specific (shNS, 5'-CCTGATATTAAGCCAT-CAAAT-3') or scrambled (shScr, 5'-TCTCGCTTGGGCGA-GAGTAAG-3') shRNAmir sequence was cloned in the TMP vector (Open Biosystems) under the control of THE promoter. An EF1a::M2 transgene was created that contains an EF 1a promoter-driven reverse Tet-transactivator (M2). Stable MDA-MB-231 clones were generated by sequential transfection of the EF1a::M2 plasmid and the TMP-shScr or TMP-shNS plasmid. Clones were selected for EF1a::M2 by G418 and TMP-shNS (or TMP-shScr) by puromycin.

Drug Treatment

Drugs tested in these studies include mycophenolic acid (Sigma, M-5255), 5-fluorouracil (Sigma, F-6627), doxorubicin (Sigma, D-1515), etoposide (E-1383), paclitaxel (Sigma, T-7402), actinomycin D (Sigma, A-9415), oxaliplatin (Sigma, 0-9512), and irinotecan (Sigma, 1-1406). Drug concentrations were described individually in each experiment.

MTT Assay

Cells were plated in 96-well plates for one day and received drug treatments for 3 days. The plating cell densities were 2,000 cells/well for human cancer cell lines, 3,000 cells/well for tumor sphere cells, and 10,000 cells/well for primary tumor cells. Following the addition of MTT solutions (10 µl, 5 mg/ml), cells were incubated for 4 hours to allow MTT to be metabolized to formazan. Formazan was then dissolved in DMSO and measured by spectrophotometer at 560 nm.

Combination Index (CI) and Isoborogram

The tumor growth-inhibitory curves of individual drugs were first measured by the MTT assay over a range of five concentrations with three-fold increment. The half-inhibitory concentrations ($IC_{50}$) were calculated by Calcusyn program (Biosoft, Ferguson, Mo.). The combined effects were measured by mixing two drugs at the 4:1, 2:1, 1:1, 1:2, or 1:4 ratio of their respective $IC_{50}$ concentrations. Each combination was tested for its tumor growth-inhibitory effect over a range of five different dosages, and calculated for its CI using the Calcusyn program. The CI values represent the averages of 3-4 independent experiments.

Immunofluorescence, BrdU Labeling, and TUNEL Assay

Primary antibodies used for immunofluorescence included rabbit anti-NS (Ab138, Cocalico), rat anti-BrdU (BU1/75, Accurate), and mouse anti-fibrillarin (38F3, EnCor) antibodies. To measure cell proliferation, cultures were treated with bromodeoxyuridine (BrdU, Accurate, OBT0030) 1 hour before harvest. Apoptotic cells were detected by the TUNEL assay (Deadend Fluoreometric TUNEL system, Promega). Images were acquired on a Zeiss LSM510 confocal microscope.

Real-time RT-PCR

The AC(t) values between the target message and two reference messages (HMG-14 and 3-actin) were determined using the MyiQ single-color real-time PCR detection system and supermix SYBR green reagent. The AAC(t) values were measured from two biological replicates and two technical repeats (n=4). Primer sequences are: SJ1, 5'-TGCCCT-TCGTCCTGGGAAAC-3' and 5'-CGCGCGCGGA-CAAACCCTT-3'; SJ2, 5'-GCGCTCTACCTTACCTAC-CTG-3' and 5'-CCGTCGGCATGTATTAGCTCT-3'; SJ3, 5'-TCGCTACTACCGATTGGATGG-3' and 5'-CTC-CGGGCTCCGTTAATGAT-3'; and 18S, 5'-GCCTGCG-GCTTAATTTGACTC-3' and 5'-CATGCCAGAGTCTCGT-TCGTT-3'.

Results

MPA Synergistically Enhances the Growth-Inhibitory Effect of 5-FU and Paclitaxel in MDA-MB-231 Cells The growth-inhibitory effect of MPA in combination with 5-FU, paclitaxel, doxorubicin (ADR), or etoposide was determined by the MTT assay in MDA-MB-231 cells. Applicants first established the $IC_{50}$ concentrations of individual agents singly by their dose response curves (data not shown). To determine whether MPA exerts a synergistic, additive, or antagonistic effect on these four drugs, Applicants used the Isoborogram software to calculate the combination index (CI) for each drug combination. For each combination, five different ratios of mixture, that is, the 4:1, 2:1, 1:1, 1:2, and 1:4 ratios, were tested, with the 1:1 ratio representing each drug at its respective $IC_{50}$ concentration. Strong, moderate, and mild synergism is defined by CI values of (0.1-0.3), (0.3-0.7), and (0.7-0.85), respectively. Additive drug interaction corresponds to CI values from 0.85 to 1. The results showed that MPA works in strong synergy with 5-FU (CI=0.047 at the 1:1 ratio), moderate synergy with paclitaxel (CI=0.3 at the 1:2 [paclitaxel:MPA] ratio), and mild synergy with ADR (CI=0.70 at the 1:1 ratio) and etoposide (CI=0.70 at the 1:1 ratio) (FIG. 1A). In MDA-MB-231 cells, the synergy of MPA on 5-FU is also significantly higher than that of oxaliplatin (OX) (CI=0.31 at the 1:2 [5-FU:OX] ratio) or irinotecan (IRI) (CI=0.37 at the 1:4 [5-FU:IRI] ratio) (FIG. 1B)-two drugs commonly used in combination with 5-FU.

MPA Significantly Enhances the Anti-Proliferative and Apoptotic Effects of 5-FU

To confirm that 5-FU and MPA act synergistically to inhibit the proliferation and induce the apoptosis of MDA-MB-231 cells, Applicants measured the percentages of BrdU- and TUNEL-labeled cells after 1 and 3 days of treatment, and compared the results between cells treated with control solution (Ctrl), 5-FU (0.15 ug/ml), MPA (0.19 uM), or 5-FU (0.15 ug/ml) plus MPA (0.19 uM). These drug concentrations represent the dosage of 5-FU and MPA that, when used in combination, yields 50% growth inhibition ($IC_{50}$) in MDA-MB-231 cells. Applicants' data showed that the 5-FU/MPA-combined treatment dramatically reduces the percentage of BrdU-labeled cells from 34.2% to 5.8% after 1 day of treatment (p<0.001) (FIG. 1C). At the selected concentrations, 5-FU or MPA alone does not decrease the proliferative rate of MDA-MB-231 cells. The TUNEL+ cells accumulate at a later time point, with the 5-FU/MPA-treated cells showing the most significant increase (FIG. 1D).

MPA and 5-FU Exhibit Cell Context-Dependent Synergy

Figure 2:
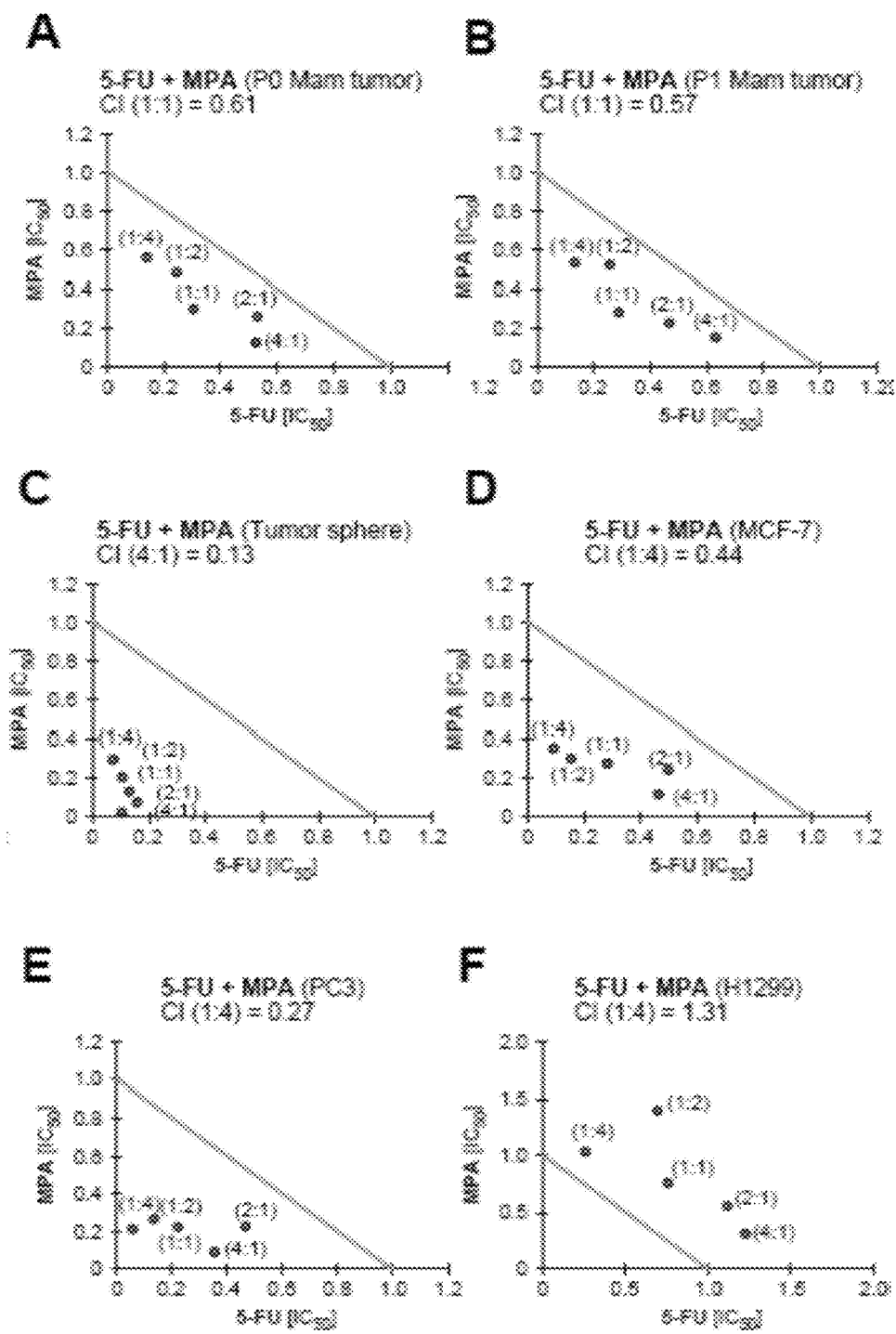
FIG. 2 provides data indicating that MPA and 5-FU show a stronger synergy in tumor sphere cells than in the total tumor cell population isolated from MMTV-wnt-1 mouse mammary tumors, and show no synergy in non-breast cancer cell types tested except for PC3 cells. Total mammary tumor cells were harvested from MMTV-wnt-1 mice and grown in adhere culture without passage (P0) or with one passage (P1). Tumor sphere cells were isolated from primary mammary tumors and maintained in suspension culture for 12-14 days. Before the drug test, sphere cells were dissociated and grown in adherent culture. 5-FU and MPA show a moderate synergistic effect against the bulk of mammary tumor cells at P0 (FIG. 2A) and P1 (FIG. 2B), and a strong synergistic effect against mammary tumor sphere cells (FIG. 2C). 5-FU and MPA show less synergistic interaction in MCF-7 cells (FIG. 2D) than in MDA-MB-231 cells. The synergistic interaction between 5-FU and MPA was tested in human prostate (FIG. 2E, PC3), lung (FIG. 2F, H1299), p53-wild-type (FIG. 2G, HCT116-8) and p53-null (FIG. 2H, HCT116-2) colorectal, bone (FIG. 2I, U2OS), and oral squamous cell (FIG. 2J, SCC-25) cancer cells using the isobologram. 5-FU and MPA show a strong synergistic effect in PC3 cells and a moderate synergistic effect in SCC-25 cells, but show no synergy in the other cell types. For SCC-25 cells, MPA also shows a strong synergistic effect of growth inhibition when used in combination with paclitaxel (FIG. 2K) or oxaliplatin (FIG. 2L).
Figure 2:
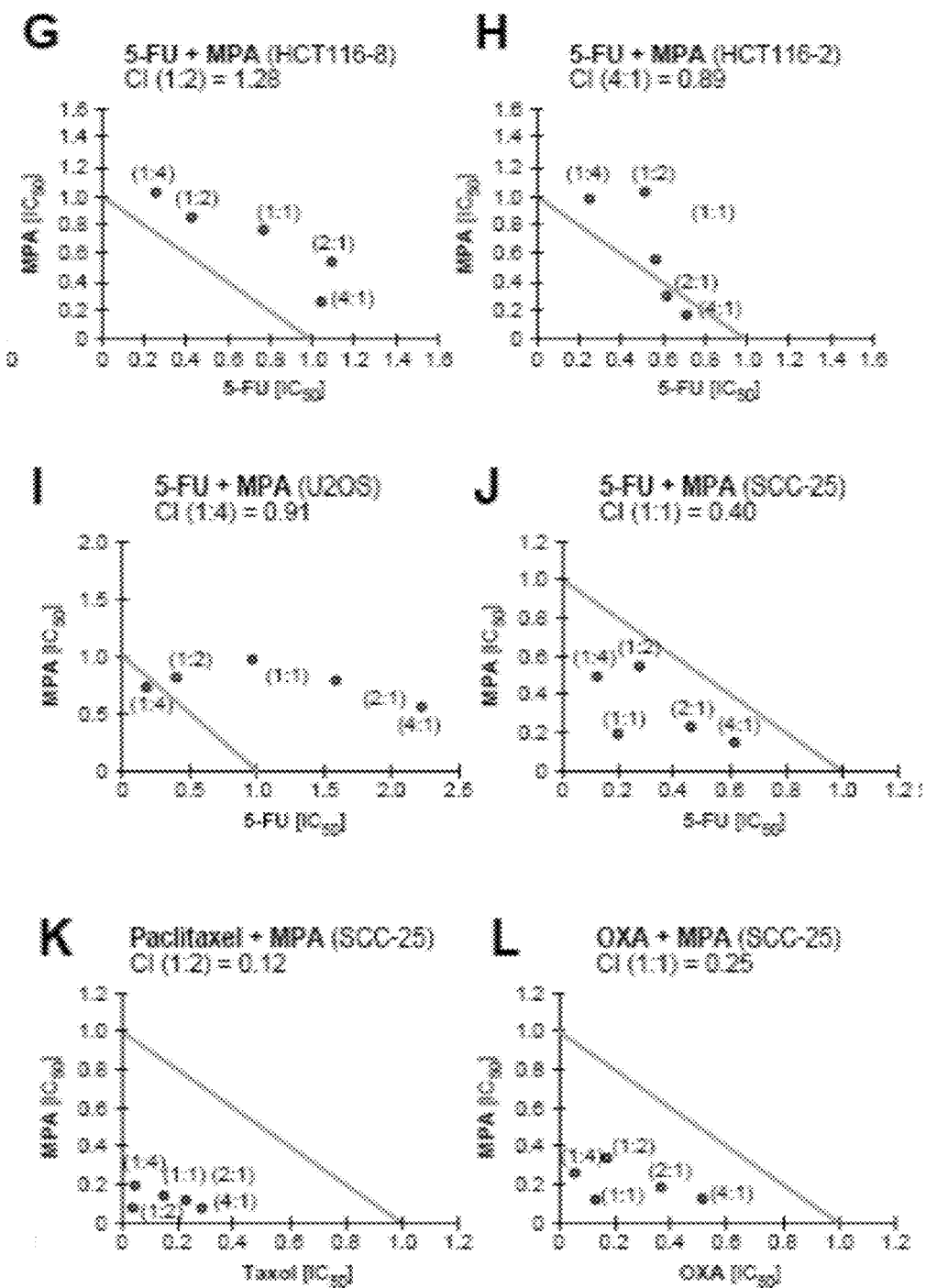

Recent studies suggest that tumor-initiating cells (TIC) may exist in solid tumors and be responsible for tumor initiation and recurrence. To compare the 5-FU/MPA synergy between the TIC-enriched cell population and the bulk of mammary tumors, Applicants isolated primary tumor cells from MMTV-wnt-1 mouse mammary tumors. The total population of tumor cells was grown in adherent culture and tested for the drug effect at passage zero (P0) and passage one (P1) (FIGS. 2A-B). TIC were enriched by the tumor sphere culture for 12-14 days, dissociated and plated as adherent culture, and tested for their response to MPA and 5-FU (FIG. 2C). Drug interaction analyses showed that the synergy between MPA and 5-FU is only moderate in the total tumor cell population at P0 (CI=0.61 at the 1:1 ratio) and P1 (CI=0.57 at the 1:1 ratio). Notably, 5-FU and MPA show a strong synergy in tumor sphere cells (CI=0.13 at the 4:1 [5-FU:MPA] ratio).

Applicants also measured the drug interaction of MPA and 5-FU in MCF-7 cells, which contain a lower percentage of $CD44^+CD24^-$ and sphere-forming cells and represent a more benign type of breast cancer cells compared to MDA-MB-231 cells. Consistent with the observations in primary tumor cells, MPA and 5-FU show only a moderate synergy in MCF-7 cells (CI=0.4 at the 1:4 [5-FU:MPA] ratio) (FIG. 2D).

Next, Applicants tested whether MPA and 5-FU can act synergistically in non-breast human cancer cells. CI analyses showed that these two drugs show a strong synergy in PC3 cells (prostate cancer, CI=0.27, FIG. 2E) and a moderate synergy in SCC-25 cells (oral squamous cell carcinoma, CI=0.4, FIG. 2J), but no synergy in H1299 (lung cancer, FIG. 2F), HCT116-8 and HCT116-2 (p53-wildtype and null colorectal carcinoma, respectively, FIGS. 2G-H), or U2OS cells (osteosarcoma, FIG. 2I). Notably, Applicants found that MPA exhibits a strong synergistic effect in SCC-25 cells when used in combination with paclitaxel (CI=0.12 at the 1:2 ratio of [paclitaxel:MPA], FIG. 2K) or oxaliplatin (CI=0.25 at the 1:1 ratio, FIG. 2L). These findings indicate that the synergy between MPA and anti-proliferative agents works in a tumor type-dependent manner.

The Synergistic Activity of MPA on 5-FU Correlates with Inhibition of Ribosome Biogenesis, but not with ADR-Induced Nucleolar Stress.

Figure 3:
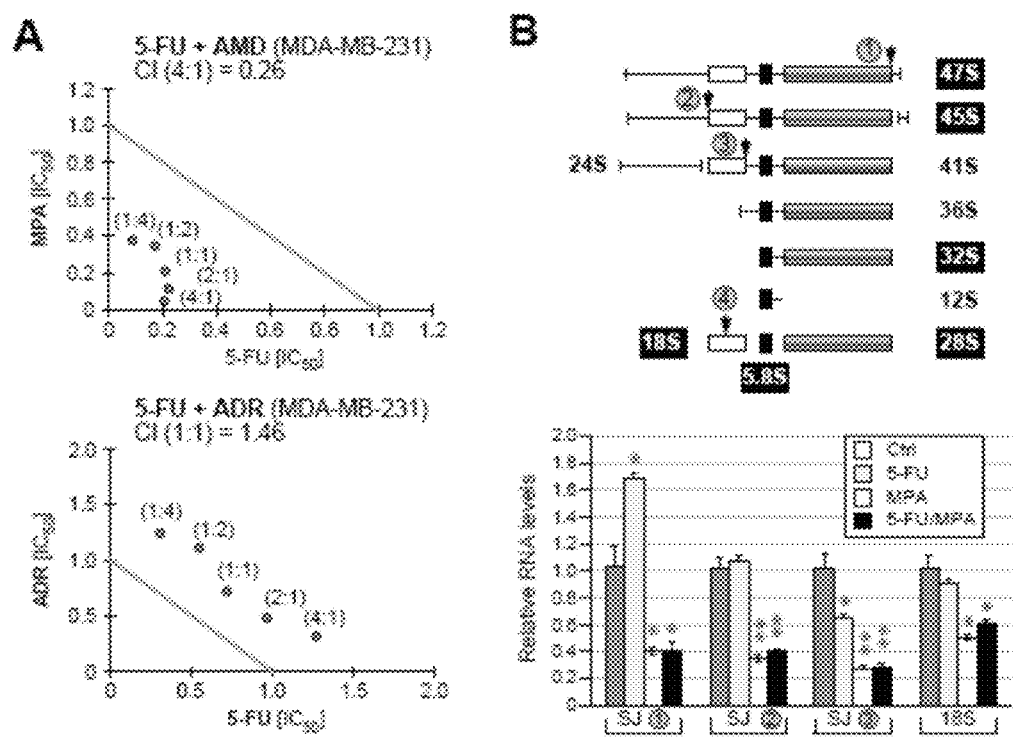
FIG. 3 illustrates that the synergistic activity of MPA on 5-FU correlates with the inhibition of ribosome biogenesis. Applicants measured the CI of 5-FU plus low-dose actinomycin D (AMD, 0.05 ug/ml) or 5-FU plus ADR (2 uM). Only AMD shows a strong synergistic effect on the anti-proliferative activity of 5-FU as MPA does (FIG. 3A). Top panel of FIG. 3B shows a schematic diagram of the ribosomal RNA (rRNA) processing step. Real-time RT-PCR primers were designed to detect pre-rRNA transcripts containing the splice junction-1 (SJ-1), SJ-2, SJ-3, or 18S rRNA sequence. Real-time RT-PCR results (bottom) showed that both MPA and the combination of MPA plus 5-FU decrease the amount of all pre-rRNA transcripts tested. 5-FU alone increases 47S pre-rRNAs and decreases the amount of SJ-3-containing transcripts (*, $p<0.01$, ; $p<0.001$; *, $p<0.0001$).

The anti-tumor activity of MPA has been linked to nucleolar stress. To investigate whether the synergy of MPA on 5-FU is related to nucleolar stress, Applicants tested the anti-tumor effect of 5-FU in combination with two inhibitors (actinomycin D [AMD] and ADR). Both drugs trigger nucleolar disassembly, but differ in that low-dose AMD (0.05 ug/ml) inhibits the activity of RNA polymerase-I, whereas ADR (2 uM) inhibits the activity of RNA polymerase-II. Applicants found that 5-FU shows a strong synergy with low-dose AMD (CI=0.26 at the 4:1 [5-FU:AMD] ratio) but not with ADR (CI=1.46 at the 1:1 ratio) (FIG. 3A), suggesting that the synergistic activity of MPA on 5-FU may be mediated by a RNA polymerase-I-dependent mechanism. To determine how 5-FU and MPA affect the synthesis or processing of pre-rRNAs, Applicants used real-time RT-PCR to measure the amounts of rRNA transcripts with the splice junction-1 (SJ-1), SJ-2, SJ-3, and 18S rRNA sequences (FIG. 3B). The results showed that MPA alone or with 5-FU can decrease the amount of pre-rRNA transcripts, including the initial precursor, 47S pre-rRNA. By contrast, 5-FU alone increases 47S pre-rRNA and decreases the amount of SJ-3-containing transcripts. These results show that the synergistic activity of MPA on 5-FU may be related to the inhibition of rRNA transcription.

Figure 4:
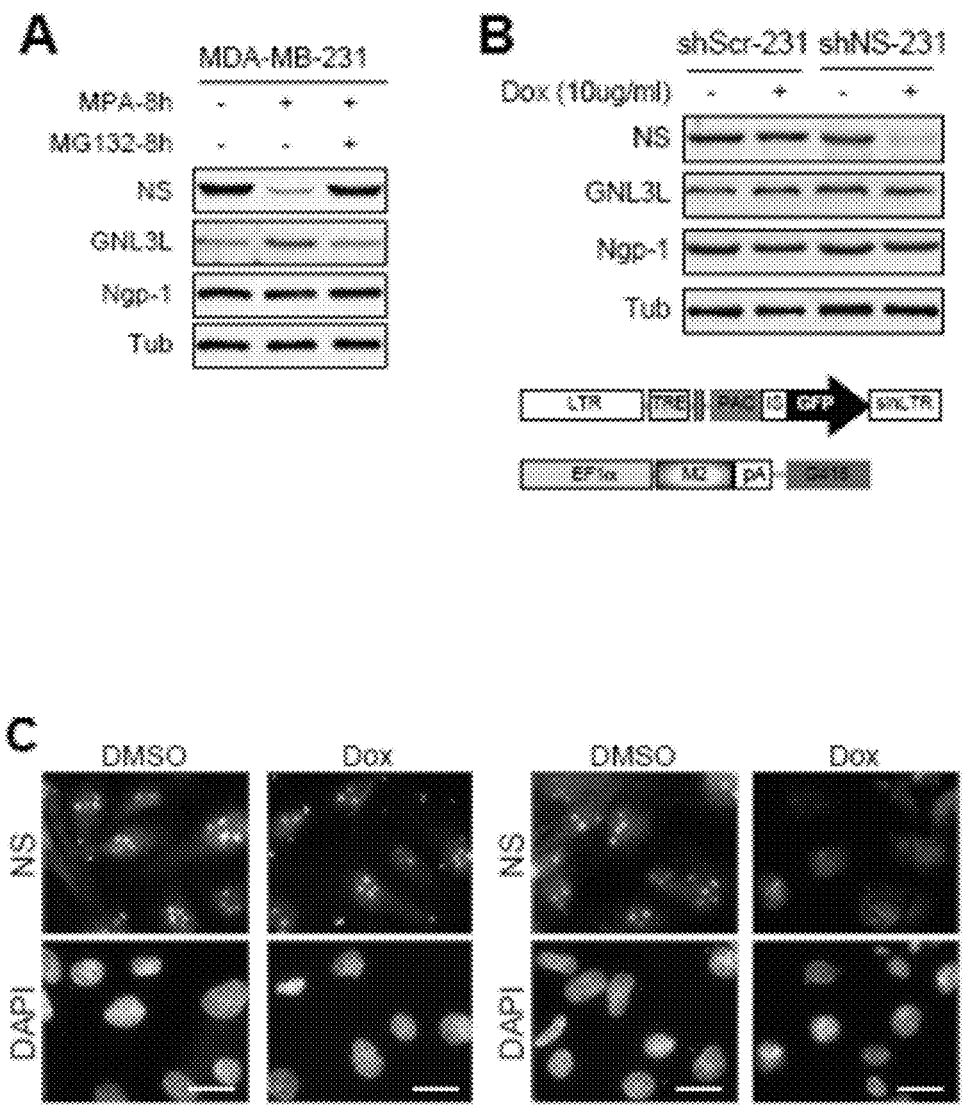
FIG. 4 shows that nucleostemin is required for the synergic activity of MPA and 5-FU in MDA-MB-231 cells. The results in FIG. 4A indicate that MPA promotes the proteasome-mediated degradation of nucleostemin protein but not GNL3L or Ngp-1 in MDA-MB-231 cells. In addition, an inducible nucleostemin-knockdown stable MDA-MB-231 cell line (231-shNS) was created by using the doxycycline (Dox)-inducible approach in conjunction with the shRNA mir-mediated knockdown strategy. Compared to the control-knockdown cells (231-shScr), Dox treatment of 231-shNS cells induces a 90% decrease of nucleostemin protein (FIG. 4B). Immunofluorescence in FIG. 4C demonstrates that the knockdown effect on nucleostemin is homogeneous. Scale bars show 20 μm. Nucleostemin-knockdown cells (Dox-treated shNS-231 cells, black bars) became insensitive to the combined therapy of 5-FU and MPA, compared to the control groups (*, $p<0.01$; **, $p<0.001$) (FIG. 4D).
Figure 4:
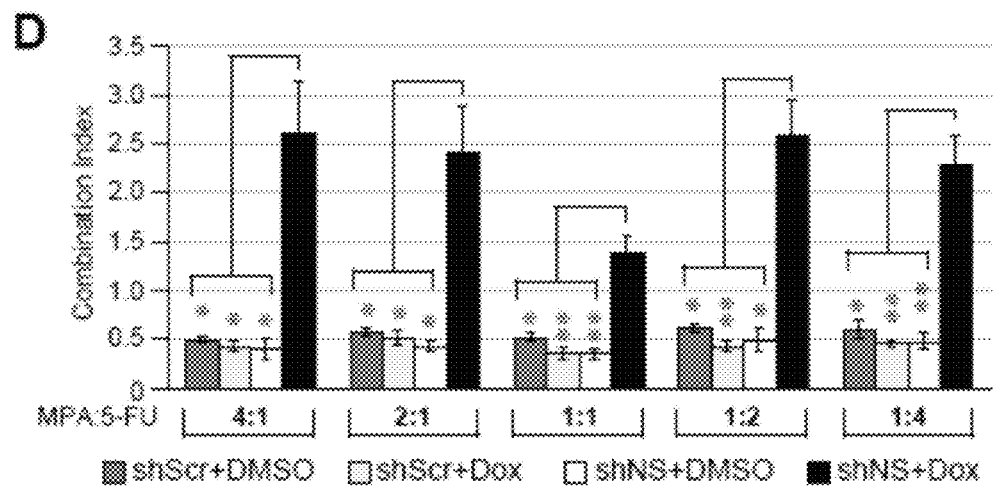

Nucleostemin is Required for the Synergy Between 5-FU and MPA in MDA-MB-231 Cells MPA has been shown to promote the degradation of a nucleolar protein, nucleostemin, which plays a crucial role in maintaining the tumorigenic activity of mammary TIC. To test the idea that nucleostemin may be involved in mediating the synergy between MPA and 5-FU, Applicants first confirmed that MPA treatment decreases the protein level of endogenous nucleostemin but not that of GNL3L and Ngp-1, the two nucleostemin homologues in vertebrate (FIG. 4A). Next, Applicants created inducible nucleostemin-knockdown (231-shNS) and control-knockdown (231-shScr) MDA-MB-231 stable cells using the doxycycline (Dox)-inducible system, and showed that Dox treatment (10 μg/ml for 3 days) induces a 90% decrease of nucleostemin protein specifically in 231-shNS cells but not in shScr cells (FIGS. 4B-C). Importantly, Applicants found that the synergistic effect of MPA and 5-FU is much higher in the control cells than in the NS-knockdown cells (Dox-treated 231-shNS cells) (FIG. 4D). The CI value of 5-FU and MPA at the 1:1 ratio is 0.52 in DMSO-treated shScr-231 cells, 0.36 in Dox-treated shScr-231 cells, 0.35 in DMSO-treated shNS-231 cells, and 1.39 in Dox-treated shNS-231 cells (p<0.01). Applicants noted that cells in the three control groups appear to be more resistant to the 5-FU/MPA-combined treatment than to the parental MDA-MB-231 cells, which may be caused by the G418/puromycin drug selection process. These results show that the synergistic effect of MPA on 5-FU in MDA-MB-231 cells may act through a nucleostemin-mediated mechanism.

Discussion

MPA Synergizes the Anti-Proliferative Activity of 5-FU in a Tumor Type-Dependent Manner Here, Applicants report a new discovery that MPA can synergistically enhance the growth-inhibitory activity of 5-FU in MDA-MB-231 cells. The synergy between 5-FU and MPA is much stronger compared to the combination of MPA and paclitaxel, ADR, or etoposide, and is also more potent than the combination of 5-FU with oxaliplatin (active ingredient of Folfox) or irinotecan. In contrast to its broad-range activity, MPA displays a high specificity in the drug (i.e. 5-FU) that it strongly synergizes with as well as in the tumor types (i.e. breast and prostate) where this particular synergy works.

Furthermore, MPA and 5-FU show differential synergy in the aggressive (e.g. MDA-MB-231 cells) versus benign human breast cancer cells (e.g. MCF-7 cells). In support, 5-FU and MPA also exert a much stronger synergistic effect in the tumor initiating cell (TIC)-enriched tumor sphere cells than in the total tumor cell population derived from primary MMTV-wnt-1 mammary tumors. These findings suggest that the combination of 5-FU and MPA can effectively target TIC population, and, therefore, may be developed into a new therapeutic option for patients with advanced breast cancers.

Potential Targets for the Synergy of 5-FU and MPA in MDA-MB-231 Cells

Figure 5:
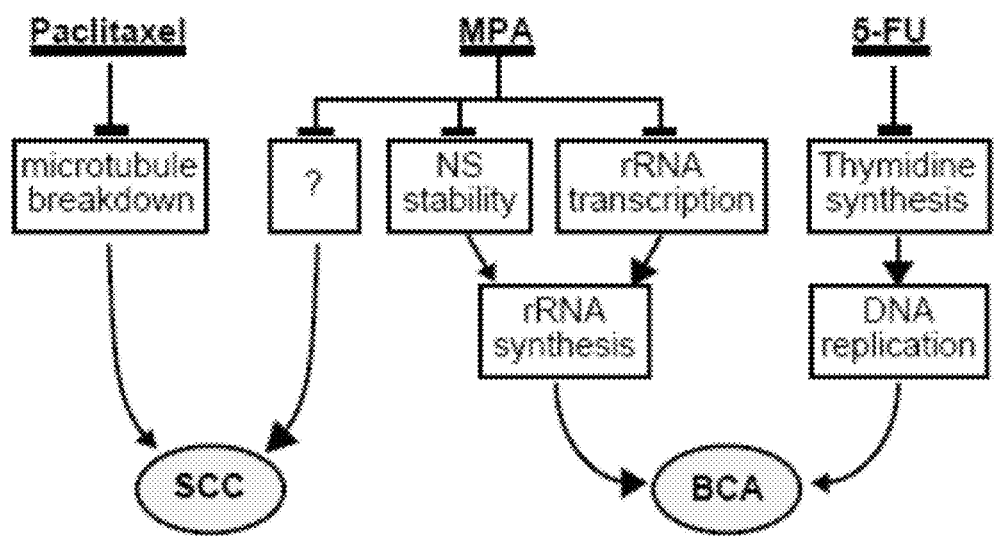
FIG. 5 provides a proposed mechanism underlying the anti-proliferative synergy of MPA in breast (BCA) and squamous cell carcinoma (SCC).

The tumor-suppressive activity of MPA has been shown to act through multiple pathways. Given that p53 is mutated in MDA-MB-231 cells and null in PC3 cells, the synergy between MPA and 5-FU should not be mediated by p53 activation. Applicants demonstrate that the synergistic effect of MPA on 5-FU depends on a nucleolar protein, nucleostemin, and can be mimicked by inhibiting the activity of RNA polymerase-I. As nucleostemin has been implicated in ribosome biogenesis and RNA polymerase-I is involved in the transcription of pre-rRNAs, one potential mechanism by which MPA enhances the activity of 5-FU may be related to the inhibition of rRNA synthesis. Supporting the idea that MPA may block the transcription of rRNA, both MPA and 5-FU/MPA-combined treatment significantly reduces the amount of $SJ-1^\pm$ transcript, which is made up by the earliest precursor in rRNA synthesis, 47S pre-rRNA. In contrast, 5-FU-treated cells show an increase in 47S pre-rRNA, suggesting that 5-FU may perturb the subsequent metabolism of 47S pre-rRNAs. Finally, MPA also triggers nucleolar disorganization. However, ADR, which is also capable of doing so, shows no synergistic effect on 5-FU. Together, and without being bound by theory, Applicants' data indicate that the synergistic activity of MPA on 5-FU may be linked to the inhibition of rRNA transcription and/or nucleostemin degradation. See FIG. 5.

MPA Synergy in Non-Breast Cancer Cells

For non-breast cancer cells, MPA and 5-FU act synergistically only in the prostate cancer (strong) and squamous cell carcinoma (moderate) but not in the lung, colorectal, and bone cancers. The lack of synergy in the lung, colorectal, and bone cancers may be related to the MPA-salvage mechanism. This cell-intrinsic salvage pathway is mediated by phosphoribosylpyrophosphate transferase (PRTase), which converts guanine to GMP and circumvents the MPA effect. Therefore, the lack of synergy of 5-FU and MPA may be explained by the different expression levels of PRTase in different tumors. Alternatively, the cell type-specific sensitivity to the 5-FU plus MPA combination may be linked to their expression levels of nucleostemin. Finally, the differential response of different cancers to the 5-FU/MPA combined therapy may indicate that tumor growth may be driven by distinct cellular pathways in different tumors, and that MPA and 5-FU may converge on the key pathway that drives the growth of breast and prostate cancer cells. Given the broad activity of MPA, it is possible that MPA may synergize other drugs in cancers that are not responsive to the 5-FU/MPA-combined treatment. Indeed, Applicants' data support this idea by showing that MPA synergistically enhances the anti-cancer effect of paclitaxel in SCC-25 cells.

Example 2

Synergistic Inhibition of Oral Premalignant Lesions

Figure 6:
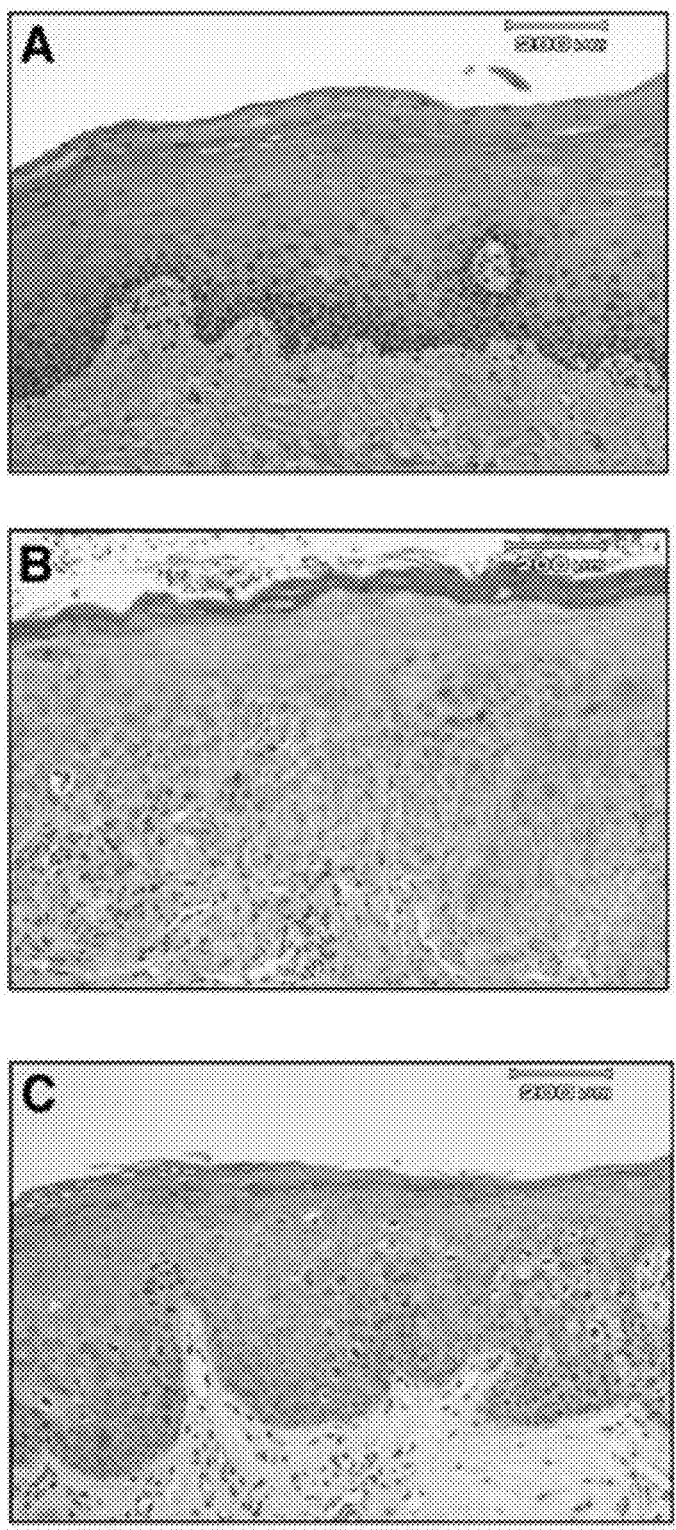
FIG. 6 provides histology of normal (FIG. 6A), moderate (FIG. 6B), and severe (FIG. 6C) oral epithelial dysplasia. Normal squamous epithelium shows small cuboid basal keratinocytes and a normal maturation pattern. Moderate epithelial dysplasia shows cellular atypia such as hyperchromatism, increased nuclear to cytoplasmic ratio, and mild pleomorphism in the keratinocytes up to the mid-portion of the epithelium. Severe epithelial dysplasia shows cellular atypia in the keratonocytes above the mid-portion of the epithelium.

Oral cancer poses a major human health issue. Pathologically, more than 90% of the oral cancers are oral squamous cell carcinomas (OSCC) that are believed to develop from clinically visible premalignant lesions, leukoplakias (white plaques) and erythroplakias (red plaques). Leukoplakias account for 85% of the oral premalignant lesions and affect as many as 1.5-4.3% of the world population. Histologically, they show hyperkeratosis and epithelial dysplasia. Depending on the involvement of histologically altered epithelial cells in the full thickness of epithelium, they are graded as mild (FIG. 6A), moderate (FIG. 6B) or severe dysplasia (FIG. 6C). The malignant transformation rate of clinically visible leukoplakia varies greatly from 0.13% to 17.5%, depending on the degree of dysplasia in the patient population. Specifically, the malignant transformation rates for moderate and severe dysplasic lesions are as high as 4-11% and 20-30%, respectively, and the actual transformation frequencies may be even underestimated by the fact that many severe lesions were treated before cancer develops.

Although some cases of mild dysplasia may regress spontaneously, the moderate and severe lesions rarely do so. This is true even for the subpopulation of tobacco-using patients who quit. Therefore, the current recommended treatment for leukoplakia with moderate and severe dysplasia is complete surgical removal.

Despite the clear indication for treating moderate and severe epithelial dysplasia, there remains no standardized treatment for these lesions to date. Current options include a combination of surgical resection, laser ablation, cryotherapy, and drugs, such as 13-cis-retinoic acid (topical and systemic), beta carotene (systemic), bleomycin (topical), and vitamin E (systemic). However, none of these treatments yields satisfactory results because the recurrence rate remains high. Furthermore, the systemic therapeutic agents are often associated with adverse side effects.

As set forth in Example 1, Applicants recently made a new discovery on a strong synergistic activity of MPA to enhance the growth-inhibitory effects of 5-FU in human breast cancer cells and of paclitaxel on oral squamous cell carcinoma cells (SCC-25). The results in Example 1 indicate that MPA may have a potent anti-cancer effect when used in combination with other anti-neoplastic agents.

In this Example, Applicants provide data regarding the clinical applicability of MPA in combination with anti-neoplastic agents for inhibiting the growth of oral pre-cancer cells, such as leukoplakias and erythroplakias.

Effect of 5-FU/MPA, Paclitaxel/MPA, and Oxaliplatin/MPA on Dysplastic Oral Keratinocytes Applicants conducted testing on the synergism between 5-FU/MPA, paclitaxel/MPA, and oxaliplatin/MPA using dysplastic oral keratinocyte (DOK) cells. See FIG. 7. Applicants determined that the $IC_{50}$ concentrations for MPA, 5-FU, paclitaxel, and oxaliplatin in DOK cells to be 6.67 uM, 1.67 ug/ml, 0.21 uM, and 0.83 uM, respectively. On the basis of the combination index (CI) of each combination, Applicants found that MPA exhibits a moderate synergistic effect when used in combination with 5-FU (CI=0.57 at a 1:1 ratio), a mild synergistic effect with paclitaxel (CI=0.81 at a 1:2 ratio of paclitaxel to MPA), and a strong synergistic effect with oxaliplatin (CI=0.039 at a 1:4 ratio of oxaliplatin to MPA). These results support the feasibility of the use of MPA and oxaliplatin or 5-FU on inhibiting the growth of DOK cells and treating oral premalignant lesions. They also indicate that the paclitaxel/MPA combination may be more optimal in some embodiments for treating oral squamous cell carcinoma than oral premalignant lesions.

Figure 7:
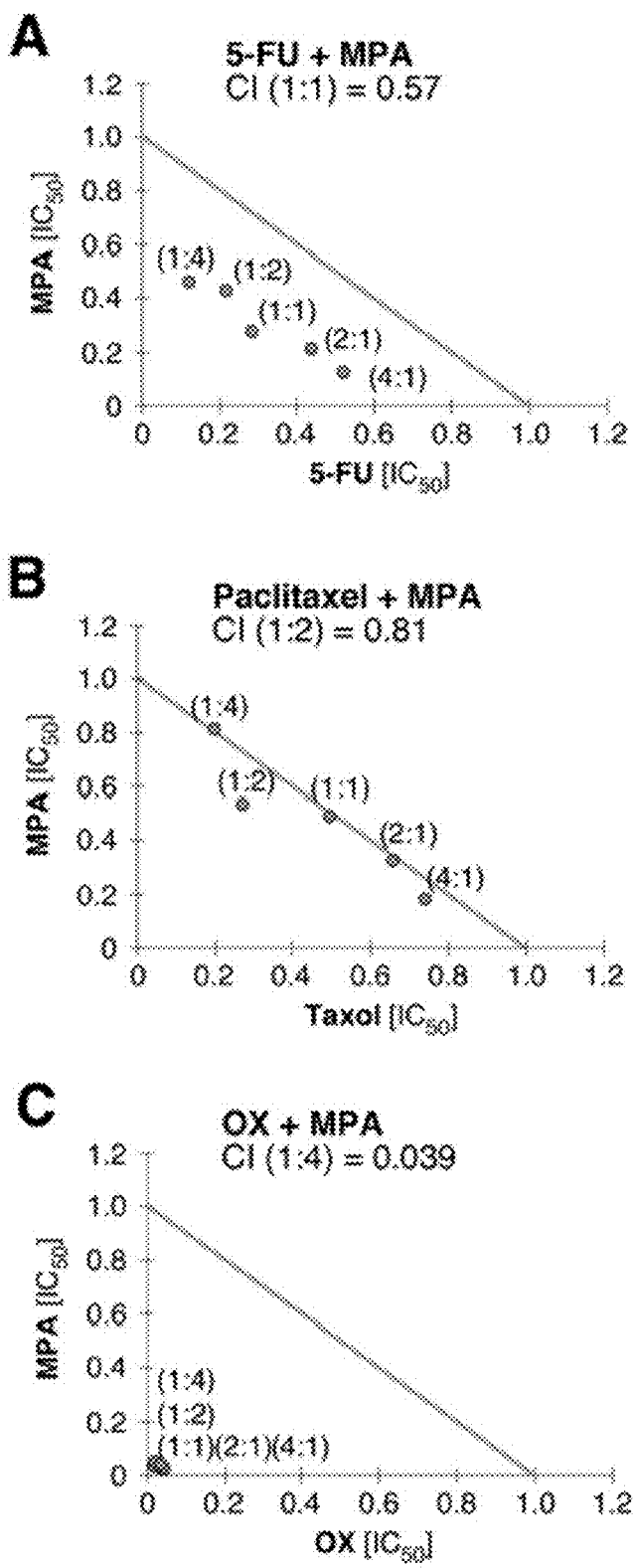
FIG. 7 shows synergistic interaction between MPA and 5-FU, paclitaxel (Taxol) or oxaliplatin (OX) on dysplastic oral keratinocytes (DOK) cells. The ability of MPA to act synergistically with 5-FU, Taxol, or OX to inhibit the growth of DOK cells was determined by their combination indices (CI). The Isobologram results demonstrate that MPA shows a moderate synergistic effect when used in combination with 5-FU (FIG. 7A, CI=0.57), a mild synergistic effect when used in combination with Taxol (FIG. 7B, CI=0.81), and a strong synergistic effect when used in combination with OX (FIG. 7C, CI=0.039).

The results shown in FIG. 7 are also consistent with Applicants' findings showing that MPA exhibits a strong synergistic effect when used in combination with oxaliplatin (CI=0.25 at a 1:1 ratio) and a moderate synergistic effect with 5-FU (CI=0.40 at a 1:1 ratio) (FIG. 2J-L). These data further support the feasibility of the use of MPA and oxaliplatin or 5-FU on inhibiting the growth of DOK cells and treating oral premalignant lesions.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of treating a tumor in a subject, wherein the method comprises:
   administering to the subject a therapeutic composition, wherein the therapeutic composition comprises:
   (a) mycophenolic acid, an analogue thereof, or a derivative thereof; and
   (b) at least one anti-neoplastic agent,
   wherein the administering comprises topical administration, and wherein the topical administration comprises the use of a topical patch.

2. The method of claim 1, wherein the tumor is associated with oral cancer.

3. The method of claim 2, wherein the oral cancer comprises oral squamous cell carcinoma.

4. The method of claim 1, wherein the tumor is associated with hyperplastic oral lesions or precancerous oral lesions.

5. The method of claim 4, wherein the tumor is associated with precancerous oral lesions, wherein the precancerous oral lesions are selected from the group consisting of leukoplakia, erythroplakia, erythroleukoplakia, and combinations thereof.

6. The method of claim 1, wherein the tumor is associated with at least one of a skin cancer, a precancerous skin lesion, or a hyperplastic skin lesion.

7. The method of claim 6, wherein the tumor is associated with skin cancer.

8. The method of claim 7, wherein the skin cancer is selected from the group consisting of squamous skin cell carcinoma, carcinoma in situ, basal cell carcinoma, melanoma, and combinations thereof.

9. The method of claim 6, wherein the tumor is associated with hyperplastic skin lesions or precancerous skin lesions.

10. The method of claim 9, wherein the tumor is associated with precancerous skin lesions, wherein the precancerous skin lesions are selected from the group consisting of actinic keratosis, actinic chelitis, cutaneous horns, warts, epidermodysplasia verruciformis, and combinations thereof.

11. The method of claim 1, wherein the subject is a human being.

12. The method of claim 1, wherein the therapeutic composition is associated with at least one carrier component, wherein the carrier component is selected from the group consisting of ointments, creams, gels, hydrogels, pastes, powders, and combinations thereof.

13. The method of claim 1, wherein the anti-neoplastic agent is selected from the group consisting of 5-fluouracil, paclitaxel, oxaliplatin, doxorubicin, etoposide, irinotecan, bleomycin, imiquimod, 13-cis-retinoic acid, and combinations thereof.

14. The method of claim 1, wherein the anti-neoplastic agent comprises oxaliplatin.

15. The method of claim 1, wherein the therapeutic composition comprises underivatized mycophenolic acid.

16. The method of claim 1, wherein the relative concentrations of the mycophenolic acid, the analogue thereof, or the derivative thereof, and the at least one anti-neoplastic agent correspond to their respective $IC_{50}$ values.

17. The method of claim 1, wherein the mycophenolic acid, the analogue thereof, or the derivative thereof, and the least one anti-neoplastic agent are present at concentrations correlating to their $IC_{50}$ values, wherein the concentration ratios of the mycophenolic acid, the analogue thereof, or the derivative thereof to the least one anti-neoplastic agent include at least one of 8 times the $IC_{50}$ value: the $IC_{50}$ value; 6 times the $IC_{50}$ value: the $IC_{50}$ value; 4 times the $IC_{50}$ value: the $IC_{50}$ value; 3 times the $IC_{50}$ value: the $IC_{50}$ value; 2 times the $IC_{50}$ value: the $IC_{50}$ value; 3 times the $IC_{50}$ value:2 times the $IC_{50}$ value; 2 times the $IC_{50}$ value:3 times the $IC_{50}$ value; the $IC_{50}$ value:2 times the $IC_{50}$ value; the $IC_{50}$ value:4 times the $IC_{50}$ value; the $IC_{50}$ value: 6 times the $IC_{50}$ value; or the $IC_{50}$ value:8 times the $IC_{50}$ value.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Neurostemin specific shRNAmir sequence

<400> SEQUENCE: 1
cctgatatta agccatcaaa t                                              21

<210> SEQ ID NO 2
<211> LENGTH: 21
<212> TYPE: DNA
<213> ORGANISM: Artificial Sequence
<220> FEATURE:
<223> OTHER INFORMATION: scrambled Neurostemin specific shRNAmir
      sequence

<400> SEQUENCE: 2
tctcgcttgg gcgagagtaa g                                              21

<210> SEQ ID NO 3
<211> LENGTH: 20
<212> TYPE: DNA
<213> ORGANISM: Artificial Sequence
<220> FEATURE:
<223> OTHER INFORMATION: splice junction-1 specific forward primer for
      18sRNA

<400> SEQUENCE: 3
tgcccttcgt cctgggaaac                                                20

<210> SEQ ID NO 4
<211> LENGTH: 19
<212> TYPE: DNA
<213> ORGANISM: Artificial Sequence
<220> FEATURE:
<223> OTHER INFORMATION: splice junction-1 specific reverse primer for
      18sRNA

<400> SEQUENCE: 4
cgcgcgcgga caaaccctt                                                 19

<210> SEQ ID NO 5
<211> LENGTH: 21
<212> TYPE: DNA
<213> ORGANISM: Artificial Sequence
<220> FEATURE:
<223> OTHER INFORMATION: splice junction-2 specific forward primer for
      18sRNA

<400> SEQUENCE: 5
gcgctctacc ttacctacct g                                              21

<210> SEQ ID NO 6
<211> LENGTH: 21
<212> TYPE: DNA
<213> ORGANISM: Artificial Sequence
<220> FEATURE:
<223> OTHER INFORMATION: splice junction-2 specific reverse primer for
      18sRNA

<400> SEQUENCE: 6
ccgtcggcat gtattagctc t                                              21

```
<210> SEQ ID NO 7
<211> LENGTH: 21
<212> TYPE: DNA
<213> ORGANISM: Artificial Sequence
<220> FEATURE:
<223> OTHER INFORMATION: splice junction-3 specific forward primer for
      18sRNA

<400> SEQUENCE: 7
tcgctactac cgattggatg g                                              21

<210> SEQ ID NO 8
<211> LENGTH: 20
<212> TYPE: DNA
<213> ORGANISM: Artificial Sequence
<220> FEATURE:
<223> OTHER INFORMATION: splice junction-3 specific reverse primer for
      18sRNA

<400> SEQUENCE: 8
ctccgggctc cgttaatgat                                                20

<210> SEQ ID NO 9
<211> LENGTH: 21
<212> TYPE: DNA
<213> ORGANISM: Artificial Sequence
<220> FEATURE:
<223> OTHER INFORMATION: Forward Primer for 18sRNA

<400> SEQUENCE: 9
gcctgcggct taatttgact c                                              21

<210> SEQ ID NO 10
<211> LENGTH: 21
<212> TYPE: DNA
<213> ORGANISM: Artificial Sequence
<220> FEATURE:
<223> OTHER INFORMATION: Reverse Primer for 18sRNA

<400> SEQUENCE: 10
catgccagag tctcgttcgt t                                              21
```